(12) United States Patent
Bates et al.

(10) Patent No.: US 7,678,118 B2
(45) Date of Patent: *Mar. 16, 2010

(54) RELEASABLE BASKET

(75) Inventors: James S. Bates, Bloomington, IN (US); James A. Teague, Spencer, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 752 days.

This patent is subject to a terminal disclaimer.

(21) Appl. No.: 11/221,831

(22) Filed: Sep. 9, 2005

(65) Prior Publication Data

US 2006/0009786 A1 Jan. 12, 2006

Related U.S. Application Data

(60) Continuation of application No. 10/356,949, filed on Feb. 3, 2003, now Pat. No. 6,942,673, which is a division of application No. 09/921,590, filed on Aug. 3, 2001, now Pat. No. 6,520,968, which is a continuation of application No. 09/583,113, filed on May 24, 2000, now Pat. No. 6,280,451, which is a continuation of application No. 09/064,704, filed on Apr. 23, 1998, now Pat. No. 6,099,534.

(60) Provisional application No. 60/060,819, filed on Oct. 1, 1997.

(51) Int. Cl.
*A61B 17/24* (2006.01)

(52) U.S. Cl. ...................................... 606/113

(58) Field of Classification Search .................. 606/1, 606/113, 114, 127, 159, 200, 210
See application file for complete search history.

(56) References Cited

U.S. PATENT DOCUMENTS

| 651,395 A | 6/1900 | Strapp |
|---|---|---|
| 2,556,783 A | 6/1951 | Wallace |
| 2,767,703 A | 10/1956 | Nieburgs |
| 3,137,298 A | 6/1964 | Glassman |
| 3,472,230 A | 10/1969 | Forgarty |

(Continued)

FOREIGN PATENT DOCUMENTS

AU 56865/86 4/1986

(Continued)

OTHER PUBLICATIONS

Vorwerk, Dierk et al., "Percutaneous Embolectomy: In Vitro Investigations of the Self-expanding Tulip Sheath", Radiology (1992) 182: 415-418.

(Continued)

*Primary Examiner*—Kevin T Truong
(74) *Attorney, Agent, or Firm*—Finnegan Henderson Farabow Garrett & Dunner, L.L.P.

(57) ABSTRACT

A medical retrieval device includes a basket formed of two or more loops. The basket may be used to retrieve material (e.g., a urinary stone) from a body. The basket opens and closes for end-encapsulation of a stone and is strengthened by support members that interconnect the basket loops. A captured stone may be released from the basket with the basket still in the body by opening the loops.

58 Claims, 14 Drawing Sheets

U.S. PATENT DOCUMENTS

| | | | |
|---|---|---|---|
| 3,828,790 A | 8/1974 | Curtiss et al. |
| 3,955,578 A | 5/1976 | Chamness et al. |
| 3,996,938 A | 12/1976 | Clark, III |
| 4,046,150 A | 9/1977 | Schwartz et al. |
| 4,198,960 A | 4/1980 | Utsugi |
| 4,243,040 A | 1/1981 | Beecher |
| 4,299,225 A | 11/1981 | Glassman |
| 4,326,530 A | 4/1982 | Fleury, Jr. |
| 4,347,846 A | 9/1982 | Dormia |
| 4,425,908 A | 1/1984 | Simon |
| 4,447,227 A | 5/1984 | Kotsanis |
| 4,557,255 A | 12/1985 | Goodman |
| 4,590,938 A | 5/1986 | Segura et al. |
| 4,611,594 A | 9/1986 | Grayhack et al. |
| 4,612,931 A | 9/1986 | Dormia |
| 4,625,726 A | 12/1986 | Duthoy |
| 4,643,184 A * | 2/1987 | Mobin-Uddin | 606/200 |
| 4,650,466 A | 3/1987 | Luther |
| 4,655,219 A | 4/1987 | Petruzzi |
| 4,682,599 A | 7/1987 | Konomura |
| 4,691,705 A | 9/1987 | Okada |
| 4,699,147 A | 10/1987 | Chilson et al. |
| 4,706,671 A | 11/1987 | Weinrib |
| 4,718,419 A | 1/1988 | Okada |
| 4,723,549 A | 2/1988 | Wholey et al. |
| 4,728,319 A | 3/1988 | Masch |
| 4,790,812 A | 12/1988 | Hawkins, Jr. et al. |
| 4,790,813 A | 12/1988 | Kensey |
| 4,794,928 A | 1/1989 | Kletschka |
| 4,807,626 A | 2/1989 | McGirr |
| 4,873,978 A | 10/1989 | Ginsburg |
| 4,885,003 A | 12/1989 | Hillstead |
| 4,893,621 A | 1/1990 | Heyman |
| 4,898,574 A | 2/1990 | Uchiyama et al. |
| 4,907,572 A | 3/1990 | Borodulin et al. |
| 4,926,858 A | 5/1990 | Gifford, III et al. |
| 4,927,426 A | 5/1990 | Dretler |
| 4,927,427 A | 5/1990 | Kriauciunas et al. |
| 4,994,079 A | 2/1991 | Genese et al. |
| 4,998,539 A | 3/1991 | Delsanti |
| 5,011,488 A | 4/1991 | Ginsburg |
| 5,030,201 A | 7/1991 | Plasestrant |
| 5,041,093 A | 8/1991 | Chu |
| 5,053,008 A | 10/1991 | Bajaj |
| 5,057,114 A | 10/1991 | Wittich et al. |
| 5,064,428 A | 11/1991 | Cope et al. |
| 5,071,407 A | 12/1991 | Termin et al. |
| 5,084,054 A | 1/1992 | Bencini et al. |
| 5,098,440 A | 3/1992 | Hillstead |
| 5,100,423 A | 3/1992 | Fearnot |
| 5,102,415 A | 4/1992 | Guenther et al. |
| 5,171,233 A | 12/1992 | Amplatz et al. |
| 5,176,688 A | 1/1993 | Narayan et al. |
| 5,192,286 A | 3/1993 | Phan et al. |
| 5,201,741 A * | 4/1993 | Dulebohn | 606/113 |
| 5,290,294 A | 3/1994 | Cox et al. |
| 5,311,858 A | 5/1994 | Adair |
| 5,329,942 A | 7/1994 | Gunther et al. |
| 5,330,482 A | 7/1994 | Gibbs et al. |
| 5,345,936 A | 9/1994 | Pomeranz et al. |
| 5,354,310 A | 10/1994 | Garnic et al. |
| 5,376,100 A | 12/1994 | Lefebvre |
| 5,421,832 A | 6/1995 | Lefebvre |
| 5,486,183 A | 1/1996 | Middleman et al. |
| 5,496,330 A | 3/1996 | Bates et al. |
| 5,499,981 A | 3/1996 | Kordis |
| 5,549,626 A | 8/1996 | Miller et al. |
| 5,562,678 A | 10/1996 | Booker |
| 5,658,296 A | 8/1997 | Bates et al. |
| 5,693,069 A | 12/1997 | Shallman |
| 5,759,187 A * | 6/1998 | Nakao et al. | 606/114 |
| 6,093,196 A | 7/2000 | Okada |
| 6,168,603 B1 | 1/2001 | Leslie et al. |
| 6,348,056 B1 | 2/2002 | Bates et al. |
| 6,350,266 B1 | 2/2002 | White et al. |

FOREIGN PATENT DOCUMENTS

| | | |
|---|---|---|
| DE | 2 020 557 A | 11/1979 |
| DE | 2821048 | 11/1979 |
| DE | 3213222 A1 | 10/1983 |
| DE | 3213223 A1 | 10/1983 |
| DE | 3407708 A1 | 9/1985 |
| DE | 3501707 A1 | 7/1986 |
| DE | 8707515 U1 | 9/1987 |
| DE | 8707516 U1 | 10/1987 |
| DE | 3620385 C1 | 1/1988 |
| DE | 3633527 A1 | 4/1988 |
| DE | 4025799 A1 | 2/1992 |
| EP | 0160870 A2 | 11/1985 |
| EP | 0 195 444 | 9/1986 |
| EP | 0 428 998 A1 | 5/1991 |
| EP | 0 737 450 A1 | 10/1996 |
| FR | 2694687 A1 | 2/1994 |
| JP | 53-126388 | 10/1978 |
| JP | 59-151949 | 8/1984 |
| JP | 62-261346 | 11/1987 |
| JP | 02-271850 | 11/1990 |
| JP | 06-502354 | 3/1994 |
| JP | 06-81507 | 11/1994 |
| WO | WO 91/11209 | 8/1991 |
| WO | WO 92/05828 | 4/1992 |
| WO | WO 94/24946 | 11/1994 |
| WO | WO 95/05129 | 2/1995 |
| WO | WO 95/08291 | 3/1995 |
| WO | WO 96/01591 | 1/1996 |

OTHER PUBLICATIONS

Vorwerk, Dierk et al., "Percutaneous Balloon Embolectomy with a Self-expanding Tulip Sheath: In Vitro Experiments", Radiology (1995) 197: 153-156.

English Translation of Official Action mailed Apr. 24, 2007 in corresponding Japanese Application 2005-513510.

English Translation of Official Action mailed Aug. 6, 2009 in corresponding Japanese Application 2007-275795.

* cited by examiner

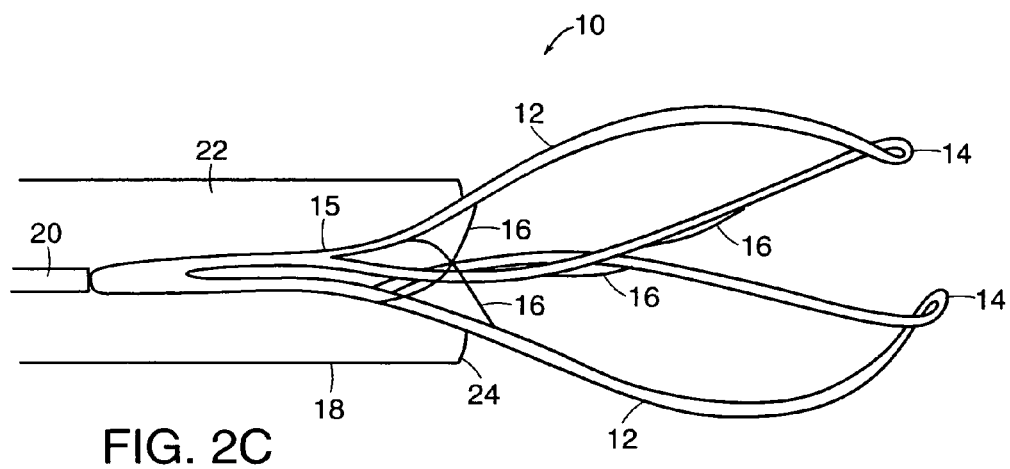
FIG. 2C
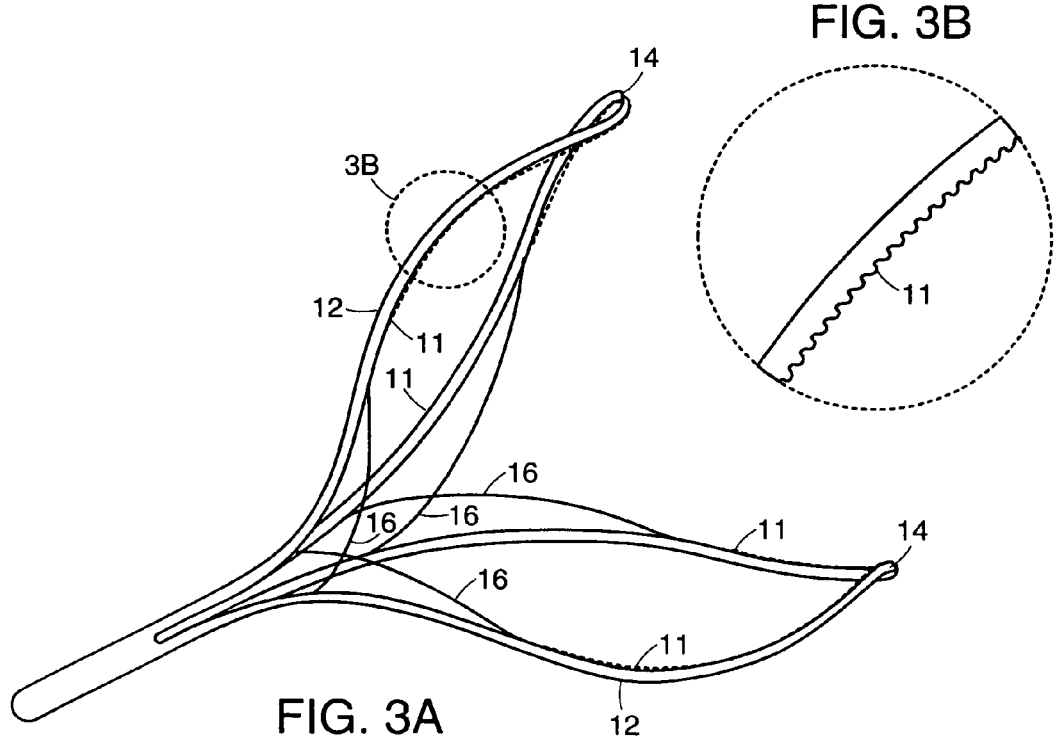
FIG. 3B
FIG. 3A

RELEASABLE BASKET

CROSS-REFERENCE TO RELATED APPLICATION

This application is a continuation of U.S. patent application Ser. No. 10/356,949, filed Feb. 3, 2003, now U.S. Pat. No. 6,942,673, which is a divisional of U.S. patent application Ser. No. 09/921,590, filed Aug. 3, 2001, (now U.S. Pat. No. 6,520,968), which is a continuation of U.S. patent application Ser. No. 09/583,113, filed May 24, 2000 (now U.S. Pat. No. 6,280,451), which is a continuation of U.S. patent application Ser. No. 09/064,704, filed Apr 23, 1998, (now U.S. Pat. No. 6,099,534), which claims the benefit of U.S. Provisional Application No. 60/060,819, filed on Oct 1, 1997, all of which are incorporated herein by reference.

TECHNICAL FIELD

The invention generally relates to medical devices such as baskets for retrieving material from within a body. More particularly, the invention relates to releasable baskets for retrieval of stones such as urinary tract stones, gall stones, and other biological materials.

BACKGROUND INFORMATION

Medical retrieval baskets generally are used to retrieve biological and foreign material from the body including stones. Such baskets may be used through an endoscope or a laparoscope, for example.

In existing medical retrieval baskets, the contour of the baskets generally are round, oval, or pear-shaped, and the baskets are formed by a plurality of legs. Stones or other biological materials are captured in the basket by moving the basket around the material to be retrieved and maneuvering the material into the basket through the space between the basket legs.

After the material is captured in a known basket, it is generally difficult to release the material from the basket if release of the captured material is required or indicated. The technical difficulty in releasing material such as a captured stone is a characteristic of known medical retrieval baskets in general. In some patients with long-standing clinical problems with urinary tract stones, a cicatrix may form in the tract as a result of trauma to its lining. The stenosis created by the cicatrix may not be so narrow so as to interfere with insertion of a retrieval basket while the basket is in a closed position. However, after the basket is expanded to capture the stone that is lodged beyond the stenotic area of the tract, the diameter of the basket containing the captured stone may exceed the diameter of the stenotic region of the urinary tract. Under these circumstances, release of the stone from the basket is a prerequisite for withdrawal of the device from the urinary tract. If the stone can not be released, more invasive, surgical approaches are required to disengage the stone from the basket.

Also, known baskets must be eased beyond the stone or to one side of the stone to permit entry of the stone into the basket. This maneuver can be technically very difficult. The narrow diameter of the tract lumen, compounded by the formation of stretch resistant scar tissue in the tract at the situs of the stone can severely limit the space around which the basket can maneuver. Moreover, the tract lining may become so attenuated at the site of the stone that advancing the basket to one side of the stone may risk rupture of the tract.

When expanded, existing baskets also generally lack dilatative strength. That is, known baskets generally are not resistive to forces countering basket expansion. The lack of dilatative strength in existing baskets is usually the result of flexible basket legs which are helpful in facilitating the entry of a stone into the basket but which decrease dilatative strength. Consequently, existing baskets generally are not effective at dilating the tract.

SUMMARY OF THE INVENTION

The invention relates to medical retrieval baskets with enhanced basket strength and with features that permit both end-encapsulation and, when indicated, release of biological material. The basic medical retrieval basket design as contemplated by the invention is an end-encapsulation basket formed by a plurality of loops supported by members disposed between the loops.

Baskets according to the invention have several advantages over other known baskets. One advantage is the feature that allows stone capture by end-encapsulation. The basket is formed by a plurality of loops, the loops are joined at the basket base, and have an unattached end at the distal portion of the basket. The basket loops are moveable between a closed position and an open position. In the open position, the ends of the loops are parted. When the basket is maneuvered into a body tract to capture material such as a stone, the basket is in a withdrawn position collapsed within the sheath. As the end of the sheath approaches the stone, the basket is extended from the sheath. The basket loops are moved between a closed position and an open position where the unattached ends of the loops are parted. With the unattached ends of the loops parted, the basket is advanced directly over the stone at the front end of the basket. The stone is end-encapsulated when the stone enters the basket through the space created by the parted unattached ends of the basket loops. The end-encapsulation basket design obviates the need for passing the basket to one side of, or beyond, the stone in order to capture the stone. The basket can "pluck" stones from embedded regions such as the calyx of a kidney. Once the stone is captured in the basket, the unattached ends of the basket loops are juxtaposed by returning the basket loops to the closed position. The stone is thereby captured and the medical retrieval device with the captured stone is removed from the body tract.

Another advantage of baskets according to the invention is that they dilate the tract. Dilation of the tract around the stone permits greater basket maneuverability thereby facilitating stone capture. Also, dilation of the tract, as the captured stone and basket are withdrawn from the tract, diminishes the potential damage that may be caused to the tract lining by ragged stone edges.

Still another advantage of a basket of the invention is the ability to release captured material. After material (e.g., a stone) is captured in the basket, the unattached ends of the basket loops may be parted by moving the basket loops from the closed position to the open position. The stone then may be released from the basket between the parted unattached ends of the basket loops.

In one aspect, the invention relates to a medical device for retrieving material from a body. The device comprises a proximal handle, a sheath, and a basket. The sheath extends distally from the handle and has a lumen extending therethrough from a distal end of the sheath to a proximal end of the sheath. The basket is moveable relative to the sheath between a withdrawn position in which the basket is collapsed within the lumen of the sheath and an extended position in which the basket extends from the distal end of the sheath and is disposed outside of the lumen. The basket has a base and a distal portion when in the extended position, and the basket comprises at least two loops which are joined at the base and which are unattached to each other at the distal portion of the basket. The loops are moveable when the basket is in the extended position between an open position and a closed position with the loops being closer together at the distal portion when in the closed position than when in the open position. This device can be used, according to another aspect of the invention, to retrieve material (biological or foreign) from a body by inserting the device, extending the basket from the sheath and moving the basket loops from a closed position to an open position, capturing the biological material within the basket, retracting the loops into the sheath wherein the unattached ends of the loops are juxtaposed thereby moving the basket to a substantially closed position, and withdrawing the basket from the body to remove the material from the body.

In one embodiment of the invention, the proximal ends of the basket loops forming the basket base are operably attached to an elongate member (e.g., a cable or wire), and the elongate member is moveable within the sheath along its length. In the withdrawn basket position, the basket is collapsed within the sheath and the unattached ends of the basket loops are together and touching. When the elongate member is advanced, the basket is extended out of the sheath moving the basket to the extended position and the unattached distal ends of the basket loops part. The basket loops thereby assume an open basket loop position by the inherent elasticity of the basket loops as movement of the elongate member causes the loops (i.e., the basket) to extend outside of the sheath. Reversing the movement of the elongate member by withdrawing it within the sheath, moves the basket loops back within the sheath and collapses them.

In another embodiment of the invention, when the basket is in the extended position, the inherent elasticity of the basket loops maintains the basket in the closed position, and wires are operably attached to an intermediate portion of the basket loops at one of the ends and to a second elongate member within the sheath by the other end. The unattached ends of the basket loops are parted when traction is applied to the second elongate member, tensing the wires, and pulling the unattached ends of the basket loops apart. The basket loops are thereby moved from a closed position to an open position.

Other embodiments of devices according to the invention include the following features. For example, a channel can be disposed through the sheath of the retrieval device, and a push rod can be axially disposed within the channel through the basket base and into the lumen of the basket. The push rod can be used to push material, such as a stone, out of the basket through the parted unattached ends of the basket loops. Furthermore or alternatively, a ram-rod or other lithotriptic device can be disposed in the channel for fragmenting the material captured and stabilized within the basket.

The basket loops can be supported by support members disposed between the loops of the basket. The support members improve the basket strength. Improved basket strength enhances stone gripping and improves dilatative force that can be exerted by the retrieval device of the invention.

Material such as mesh or woven material may be disposed in the loops of the basket. The basket loops with the disposed material within the loops may form opposing concave or cuplike structures for holding the captured material.

At least a portion of at least the inner surfaces of the basket loops can be modified to improve stone gripping. For example, all or a portion of the inner surfaces of the loops can be coated with an anti-slip substance such as a rubberized material or roughened in some manner (e.g., by serrations, abrasions, etching, etc.) to increase friction between the inner surfaces of the basket loops and the captured material.

It is possible with baskets according to the invention to remove polyps such as gastrointestinal polyps. In such embodiments, the basket loops are energized (e.g., with electrical energy such as RF energy) to excise a polyp. Also or alternatively, the basket loops may have a cutting surface. Polypectomy may be performed and the polyps preserved in the basket for subsequent pathological examination.

The invention also contemplates methods related to the baskets such as methods for constructing the basket loops from a single piece of material a flat, substantially oval, symmetrical template. The template has oppositely disposed ends and is removed from the single piece of material. As part of the manufacturing process, the material is subsequently bent and folded to form the basket structure. The bends and folds provide elasticity to the opposed loops. The elasticity introduced by folding and bending the basket materials is taken advantage of to open and close the basket loops.

In another aspect of the invention, a method for manufacturing a medical retrieval basket comprises removing a flat, substantially oval template from a single piece of construction material. The template is symmetrical and has a first end and a second end, with the first and second ends being oppositely disposed. The template is then folded such that the first and second ends of the template are brought together, and the joined ends are then secured together.

BRIEF DESCRIPTION OF THE DRAWINGS

In the drawings, like reference characters generally refer to the same parts throughout the different views. Also the drawings are not necessarily to scale, emphasis generally being placed upon illustrating the principles of the invention.

FIG. 2C is a plan view of the device with the basket in an intermediate position between closed and open (FIG. 2B).

FIG. 3A is a plan view of basket loops according to the invention illustrating a modification of the inner surface of the basket loops.

FIG. 3B is an expanded view of a section of a basket loop shown in FIG. 3A.

DESCRIPTION

Figure 1A:
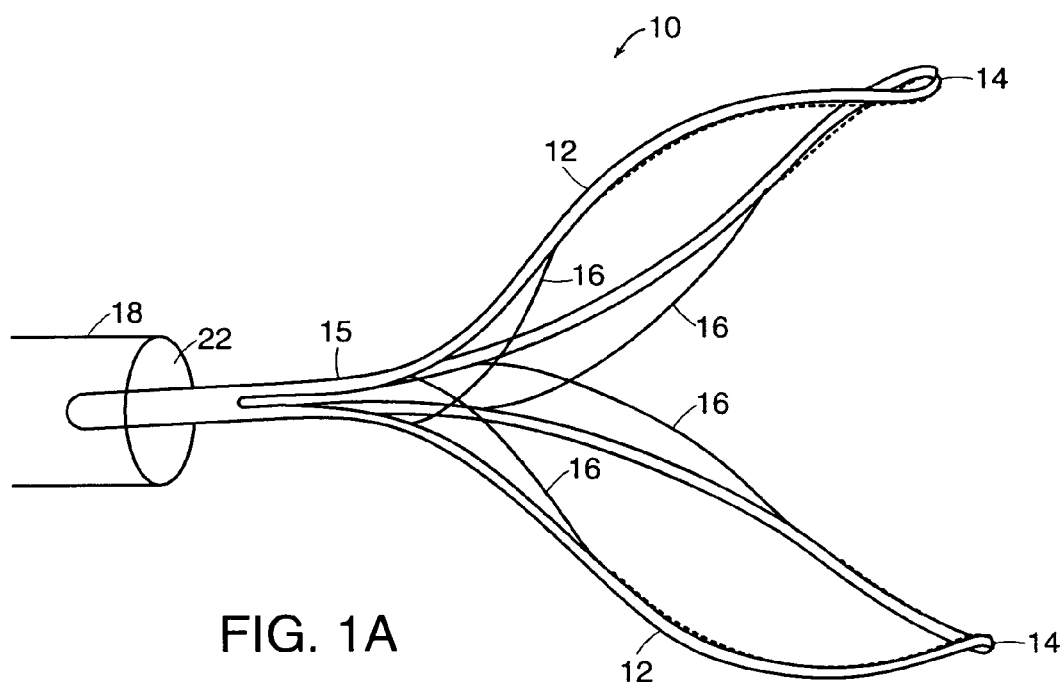
FIG. 1A is a plan view of a medical retrieval device according to the invention with the basket in the open position.
Figure 1B:
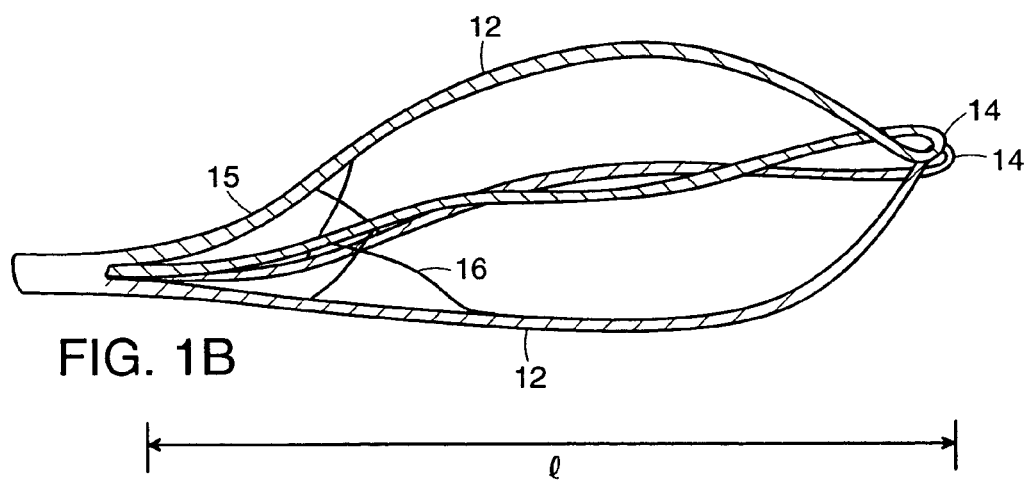
FIG. 1B is a plan view of the medical retrieval device of FIG. 1A with the basket in the closed position.
Figure 1C:
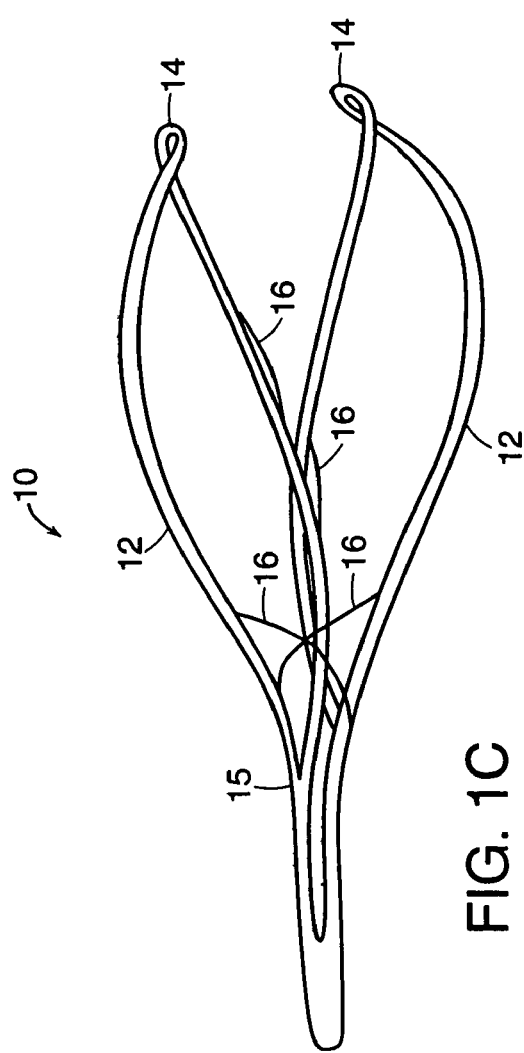
FIG. 1C is a plan view of a medical retrieval device with the basket in an intermediate position between closed (FIG. 1B) and open (FIG. 1A).
Figure 1D:
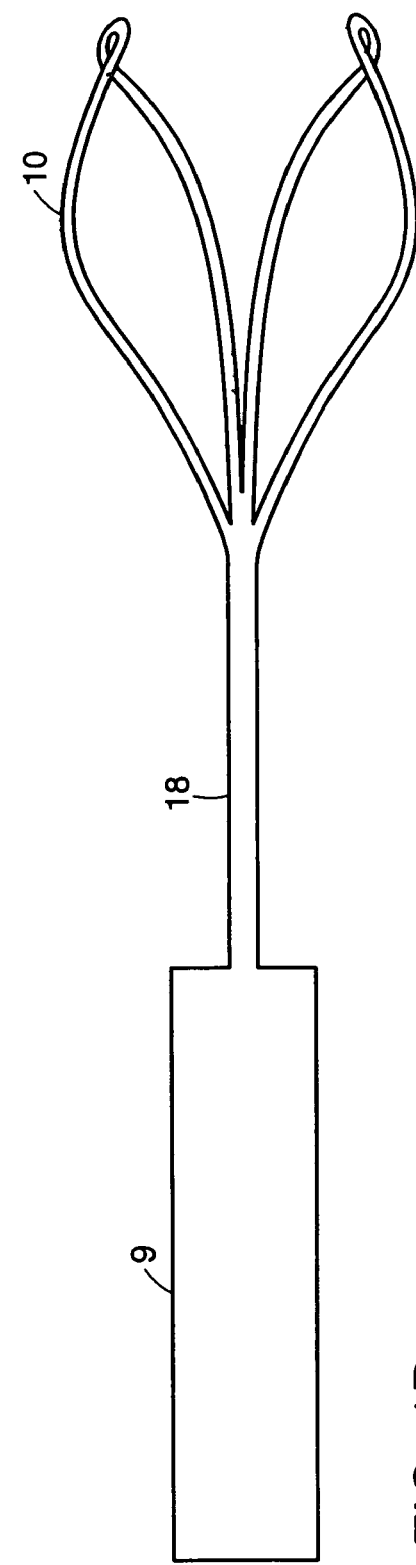
FIG. 1D shows a medical retrieval device according to the invention including a distal basket, an intermediate sheath, and a proximal handle.

Referring to FIGS. 1A and 1D, a retrieval device according to the invention includes basket 10, a catheter or sheath 18 for introduction of the basket 10 into a tract, and at least one cable 20 extending and moveable within the sheath 18. As shown in FIG. 1D, the device also includes a proximal handle 9 at the proximal end of the sheath 18, and this handle typically includes one or more actuating mechanisms (e.g., a slide, a knob, a dial, etc.) coupled to the sheath 18 and/or the cable 20 for causing the sheath 18 and the basket 10, under operator control, to move relative to each other to move the basket from a collapsed position within the sheath to an extended position outside of the sheath. The cable 20 generally can be any elongate member such as a cable, wire, coil, or shaft, for example. The basket 10 includes at least two basket loops 12. Each of the basket loops 12 has an unattached end 14 and a base or a fixed end 15.

The basket 10 is moveable between an open position and a closed position. In FIG. 1A, the basket 10 is in an open position. When the basket 10 is in the open position, the unattached ends 14 of the basket loops 12 are parted as shown in FIG. 1A. When the basket 10 is in the closed position, as shown in FIG. 1B, the unattached ends 14 of the loops 12 are juxtaposed in that they are located close together. The basket 10 may assume any position between the open and closed positions. For example, the unattached ends 14 of the basket loops 12 may be parted to any intermediate position along an arc drawn by the unattached ends 14 of the basket loops 12 as the loops move between the closed position illustrated in FIG. 1B and the open position illustrated in FIG. 1A. FIG. 1C illustrates an exemplary intermediate position of the unattached ends 14 of the basket loops 12 between the open position of the basket 10 and the closed position of basket 10.

The basket loops 12 may be any shape, for example, generally oval (as shown in FIG. 1A), round, oblong, or asymmetrical. The basket loops 12 may be disposed in one or more planes as shown in FIG. 1A. Also, while two loops 12 are shown and described herein, it is possible to construct a device with two or more loops 12 and such devices are within the scope of the invention. For example, a device with three or four or more loops 12 is possible.

Also, the length of each of the loops 12 (l in FIG. 1B) can be the same, or one can be slightly longer than the other such that the ends 14 do not exactly align upon closure. Having one loop longer than the other has been shown to help in collapsing the basket to its smallest profile such that it fits into a sheath 18 (FIG. 2A) easier.

Referring still to FIG. 1A, in a disclosed embodiment, the basket loops 12 are strengthened by support members 16. The support members 16 are struts disposed between the two opposing basket loops 12. The support members 16 or struts help to prevent scissoring of the basket loops in a horizontal plane and add strength to the basket in a vertical plane when the basket is expanded. It is possible to achieve a functioning basket without the members 16.

Figure 2A:
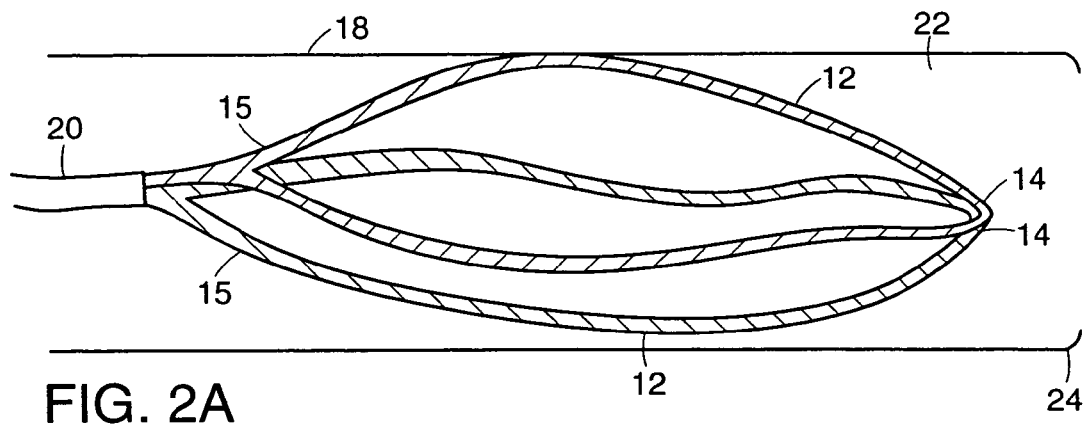
FIG. 2A is a plan view of a medical retrieval device with the basket in a collapsed position within the sheath.
Figure 2B:
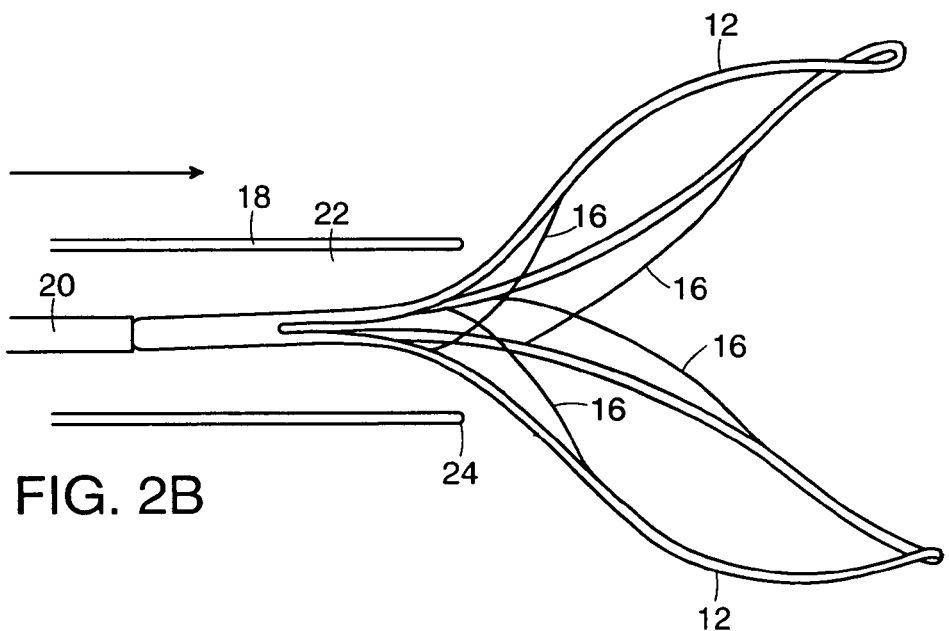
FIG. 2B is a plan view of the device of FIG. 2A with the basket in an open position and extended outside of the sheath.

Referring to FIG. 2A, in one embodiment of the invention, the base 15 of the basket 10 is operably attached to a first cable or elongate member 20 axially disposed within the lumen 22 of the sheath 18. The basket 10, when retained within the lumen 22 of the sheath 18, is in the collapsed position. In one embodiment, the sheath is made of an biologically inert, generally flexible material. Referring to FIG. 2B, advancing the first cable 20 in the direction of the arrow extends the basket 10 from the end 24 of the sheath 18. In this embodiment, the elasticity of the basket loops 12 causes the loops to part at their unattached ends 14 thereby moving the basket from a closed position to an open position.

The basket 10 may assume any position between a closed position and an open position depending on the extent the basket has moved beyond the end of the sheath. For example, the basket may assume the intermediate position, illustrated in FIG. 2C. The ends 14 of the basket loops 12 may assume any position on an arc drawn by the unattached ends 14 of the basket loops 12 as the basket extends from fully out of the sheath to fully withdrawn within the sheath.

In the disclosed embodiment, the basket loops 10 are made from a metal material. For example, basket loop material can be specialty metals such as 455 custom stainless steel or NiTi ("Nitinol"). Alternatively the basket loops can be made from plastic, a composite, polymer, or other material. Also, the basket loops may be formed from laminations of the above materials. In the disclosed embodiment, the basket loops are made of flat wire (i.e., wire that is rectangular in cross section) that is about 0.003 to 0.005 inches thick, but may be of a round, D-shape, or other cross-sectional shape.

Referring to FIG. 3A, the basket loops can have an inner surface 11 that is designed to maximize grip on material. In one embodiment, as shown in FIG. 3B, at least a portion of the inner surface 11 is roughened by serrations or teeth. Roughening can also be achieved on the inner surfaces by etching, points, or a variety of other means. One or more of the basket loops may have such a rough inner surface, and it may cover all or a portion of one or more of the inner surfaces.

Figure 4A:
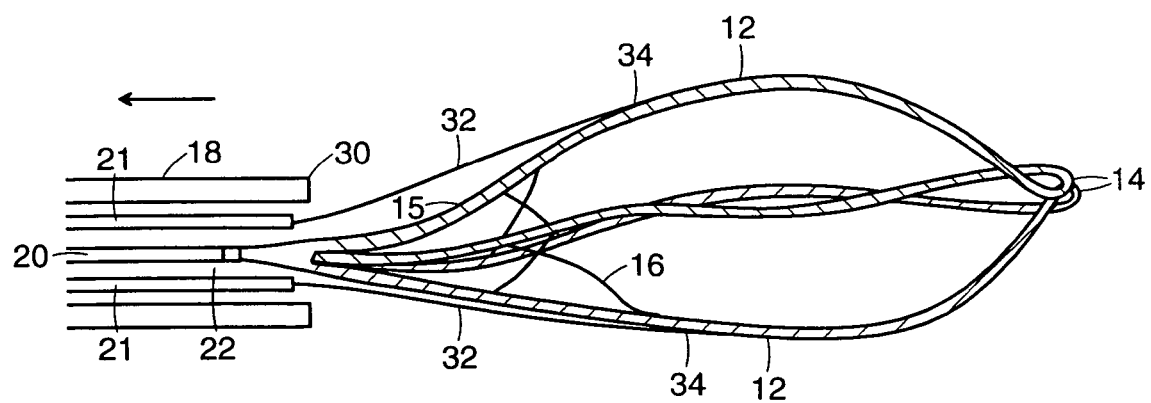
FIG. 4A is a plan view of a basket of the invention in the closed position illustrating second elongate members.

Referring to FIG. 4A, in an alternate embodiment, when the basket 10 is extended from the sheath 18, the basket maintains a closed position. In this alternate embodiment, an end of at least one wire 32 is operably attached to an intermediate portion 34 of at least one of the basket loops 12. The wire extends into the lumen 22 of the sheath 18 and is operably attached by its other end to a second cable or elongate member 21 disposed within the lumen 22 of the sheath 18. The second cable 21 may be disposed in the same or different lumens as the first cable 20. The wire 32 is kept taut by traction on the second cable 21 supplied by a mechanism at the proximal handle of the device.

Figure 4B:
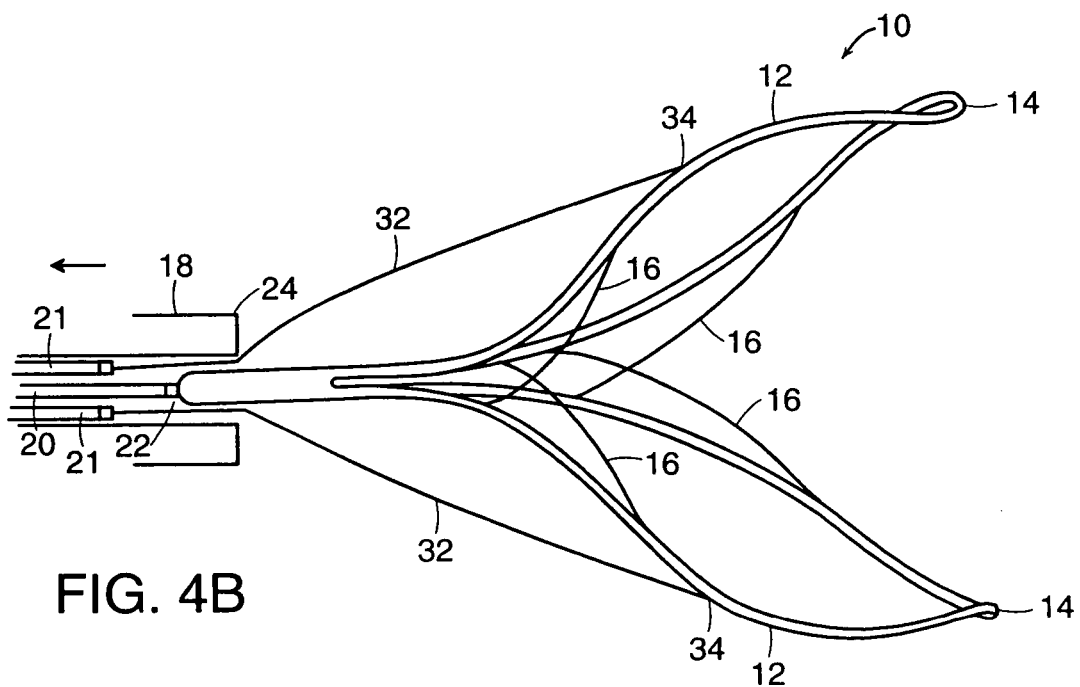
FIG. 4B is a plan view of a basket of the invention in the open position illustrating second elongate members.

With continued reference to FIG. 4A, when the second cable 21 is axially moved in the sheath lumen 22 in the direction indicated by the arrow, the tension on the wires 32 is increased and the ends 14 of the basket loops 12 move apart until the basket is in an open position as illustrated in FIG. 4B. The position of the basket 10 may be additionally fine-tuned by axial movement of first cable 20. The ends 14 of the basket loops 12 may assume any position along an arc drawn by the ends 14 of the basket loops 12 depending on the degree of tension imparted to the wires 32 by the traction maintained on second cable 21 and first cable 20.

Figure 4C:
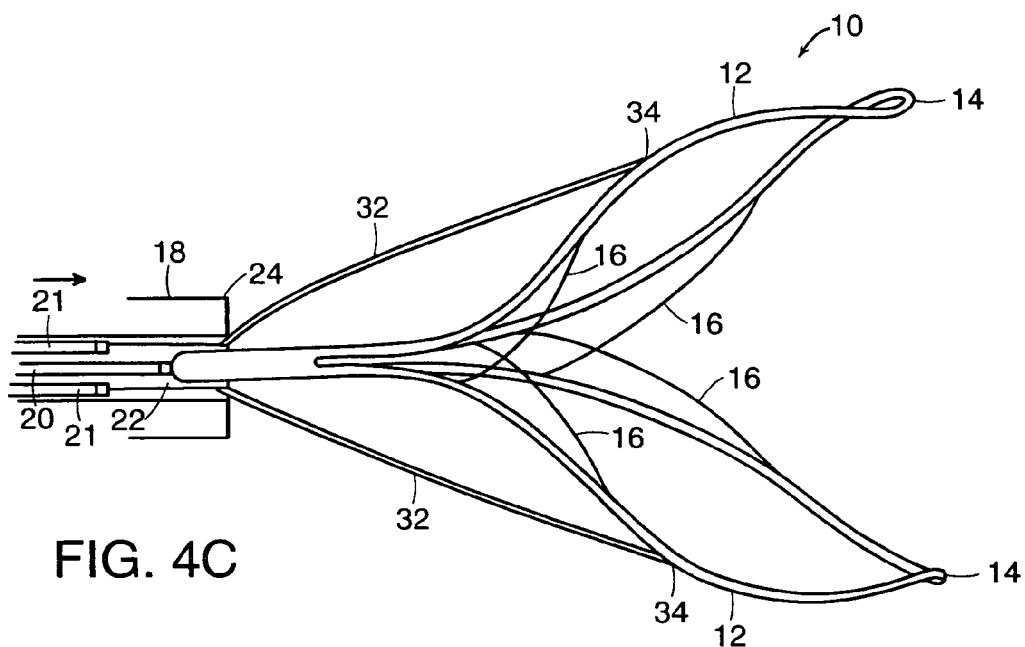
FIG. 4C is a plan view of a basket of the invention in the open position illustrating rigid second elongate members.
Figure 4D:
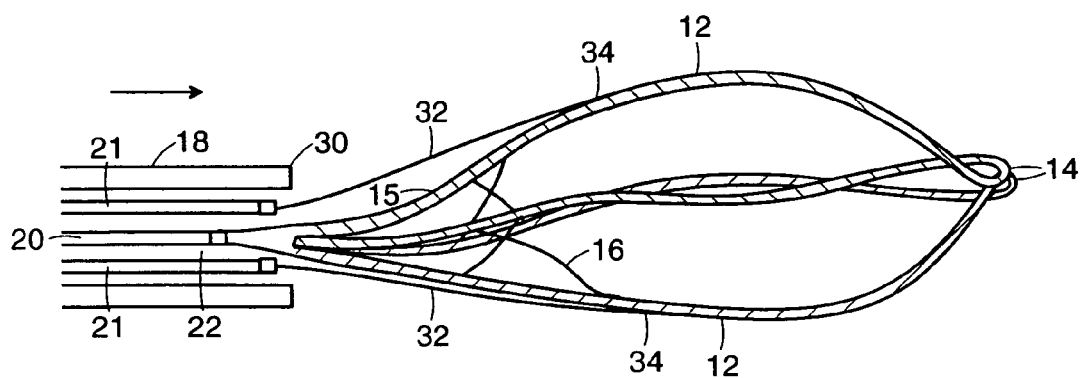
FIG. 4D is a plan view of a basket of the invention in the closed position illustrating rigid second elongate members.

Referring to FIG. 4C, in another embodiment of the invention, when the basket 10 is extended from the sheath 18, the basket 10 assumes an open position. In this embodiment, the wires 32 are formed of stiff material. To move the basket from an open to a closed position, the first cable 21 is advanced in the direction of the arrow. The stiff wires 32 push the basket loops ends 14 closer together thereby moving the basket from an open to a substantially closed position as shown in FIG. 4D. Further fine adjustment to the basket can be made by axial movement of first cable 20.

In other embodiments of the invention, the device includes two or more basket loops and at least one wire operably attached to at least one of the two or more basket loops.

Figure 5A:
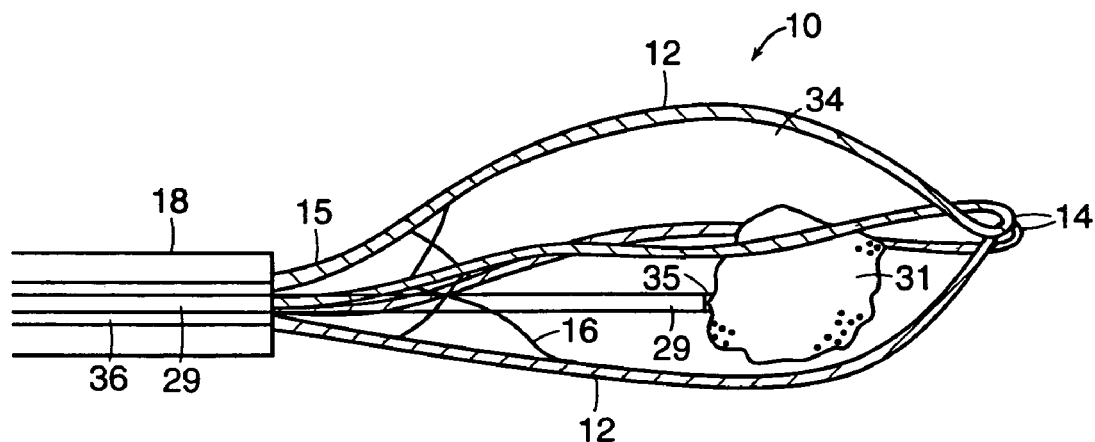
FIG. 5A is a plan view of an embodiment of a basket according to the invention including a lithotriptic device.

Referring to FIG. 5A, in another embodiment of the invention, a channel 36 is longitudinally disposed within the sheath 18 and extends through the fixed end 15 of the basket loops into the lumen 34 of the basket 10. A ram-rod 29 or other lithotriptic device such as, for example, a laser, is longitudinally disposed in the channel 36. In operation, a stone 31 is captured in the lumen 34 of the basket 10. The ram-rod 29 is advanced in the channel beyond the fixed ends 15 of the basket loops and into the lumen 34 of the basket 10 until the end 35 of the ramrod 29 abuts the stone 31. The stone 31 is then fragmented by lithotripsy. The fragmented stones 31 are withdrawn from the tract while encapsulated in the basket.

Figure 5B:
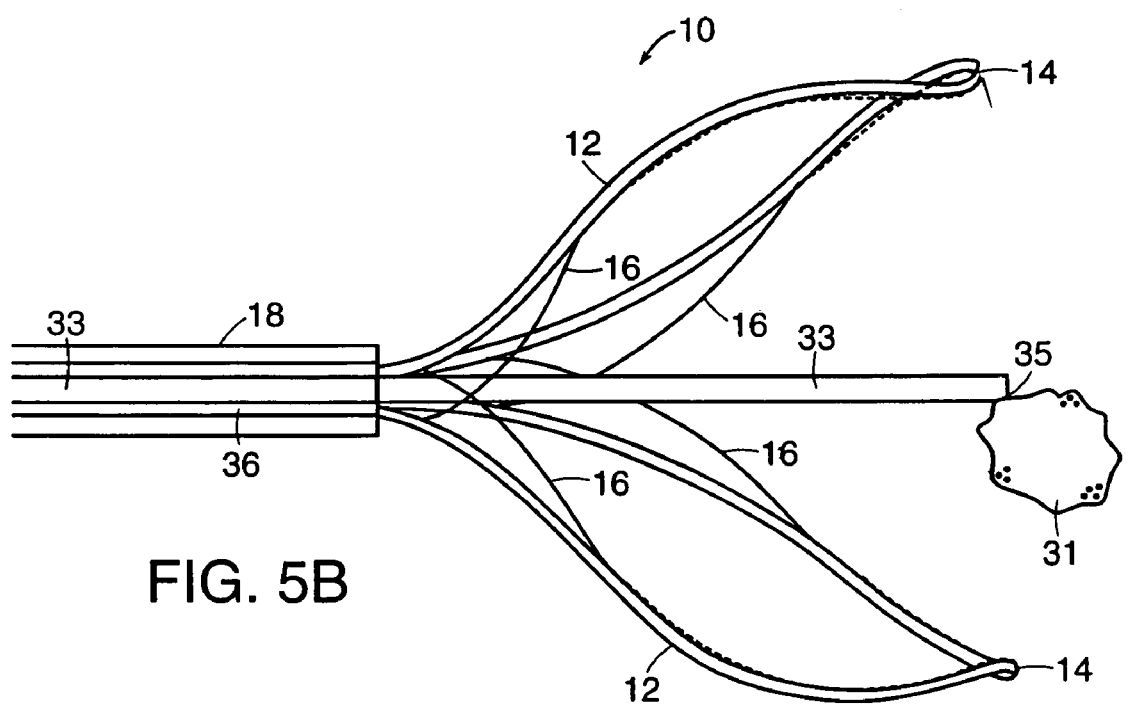
FIG. 5B is a plan view of an embodiment including a push rod.

Referring to FIG. 5B, in an alternate embodiment of the invention, after fragmentation of the stone, or under circumstances in which it is desirable to release the stone from the basket, the basket 10 is moved from the closed position to the open position. A push rod 33 disposed within the channel 36 is advanced into the lumen 34 of the basket until the end 35 of the push rod 33 contacts the stone or stone fragment 31. The push rod 33 is advanced further into the lumen 34 of the basket 10 until the stone or stone fragment 31 is pushed out of the basket lumen 34 through the parted ends 14 of the basket loops 12.

Figure 6:
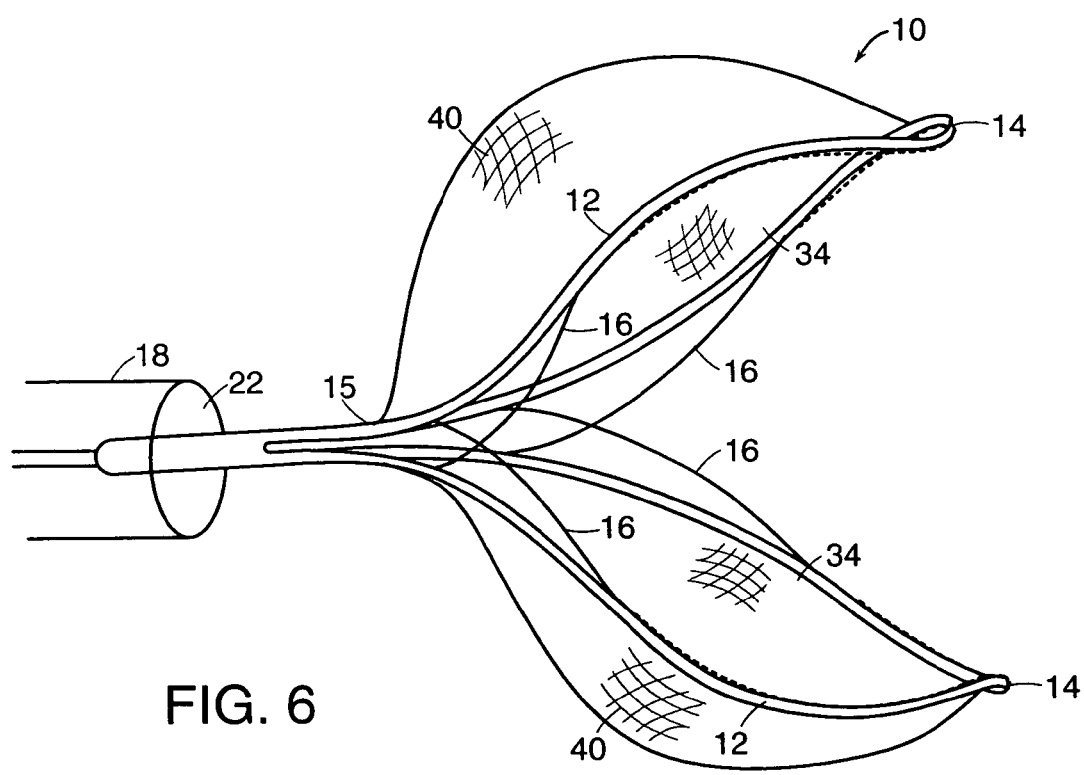
FIG. 6 is a plan view of a device having a mesh disposed within the basket loops.

Referring to FIG. 6, in yet another embodiment of the invention, the basket loops 12 have a membrane or mesh material 40 disposed within the loops 12. The basket loops 12 serve as a frame to support the mesh or membrane. The mesh or membrane 40 is attached to the wire loop frame by any means known to one skilled in the art. In one embodiment, as illustrated in FIG. 6, the mesh or membrane 40 of the loops 12 form a concavity so that the lumen 34 of the basket is a pocket or is cup-shaped. The mesh or membrane 40 can be formed of polymer, membrane, wire, metal, mesh, film, cloth, fabric, textile, woven material, etc.

Figure 7A:
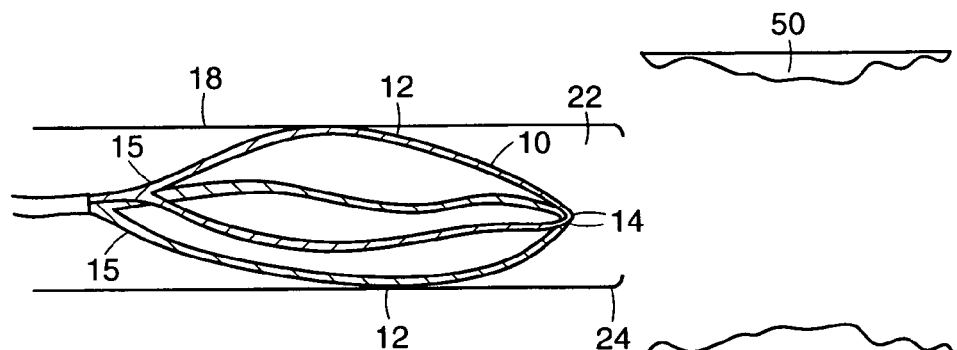
FIGS. 7A-7D are diagrammatic representations of a clinical application of the device of FIGS. 2A, 2B, and 2C.
Figure 7B:
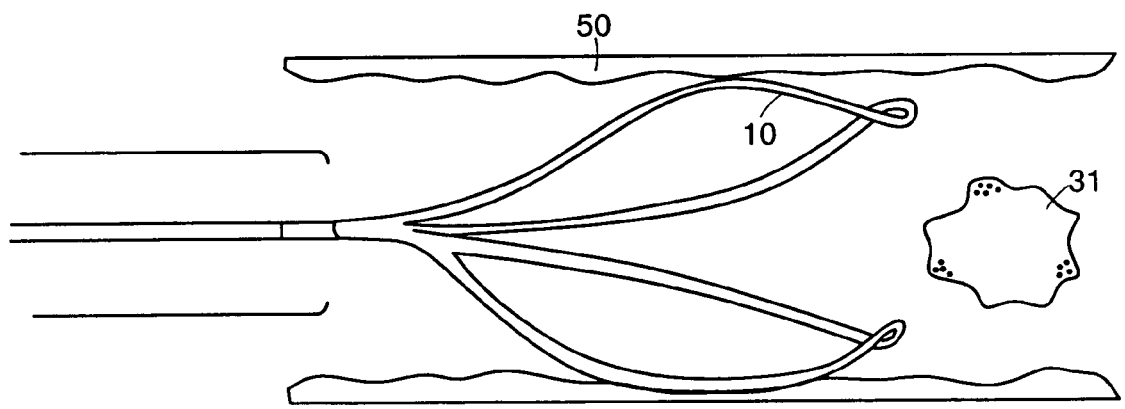
Figure 7C:
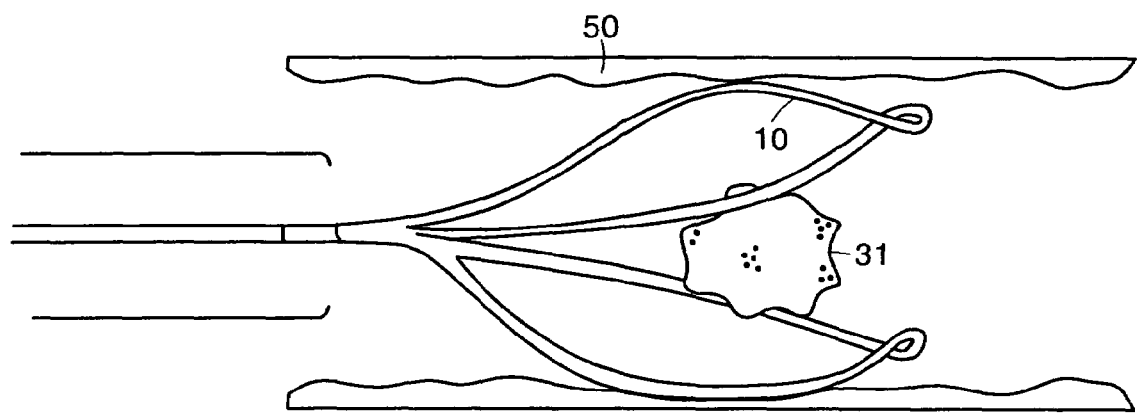
Figure 7D:
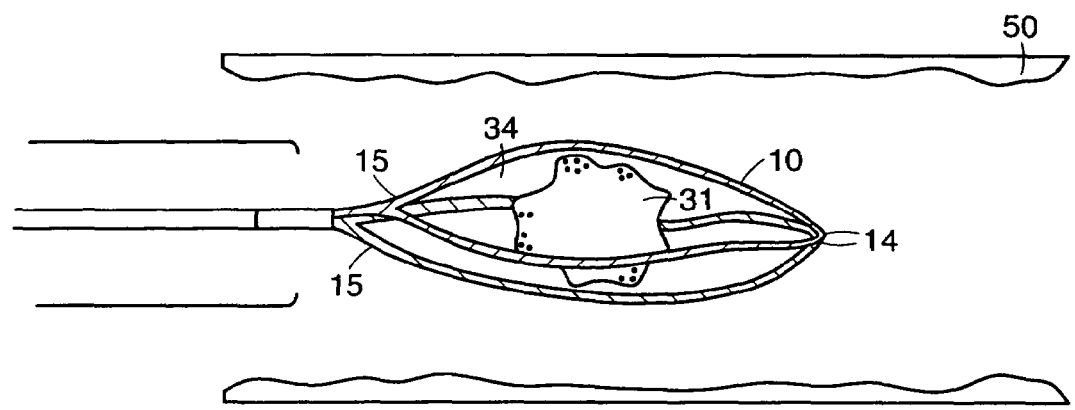

In operation, referring to FIG. 7A, the retrieval device is inserted into a tract 50 of the body to retrieve biological material, for example, a stone in the gall bladder, biliary tree, ureter, kidney, or urethra. The end of the device 24 is inserted into the tract 50 while the basket 10 is collapsed and enclosed within the sheath 18. Referring to FIG. 7B, the basket 10 is advanced in the body tract 50 until the end of the basket 24 approaches the stone 31. As the basket approaches the stone 31, the basket 10 is extended out of the sheath and moved from a collapsed position to an open or intermediate position. The method of opening and closing the basket does not substantially alter the operation of the device in capturing a stone within a tract. Referring to FIG. 7C, the basket 10 is advanced further into the body tract 50 until the stone 31 is captured by end-encapsulation. End-encapsulation occurs when the stone 31 passes between the parted unattached ends 14 of the open basket 10. Referring to FIG. 7D, after the stone 31 is positioned within the lumen 34 of the basket 10, the basket 10 is returned to a closed position. The unattached ends 14 of the basket loops 12 are substantially juxtaposed entrapping the stone 31 within the basket 10. It is not essential to the operation of the basket that the unattached ends 14 of the basket loops 12 actually meet. For particularly large stones, for example, the diameter of the stone will prevent juxtaposition of the unattached ends of the basket. However, the essential feature of successful end-encapsulation for stone removal is sufficient contact between the inner surface of the basket loops with the stone surface so that the stone does not inadvertently slip out of the basket. The retrieval device with the entrapped stone is withdrawn from the body tract.

Figure 8A:
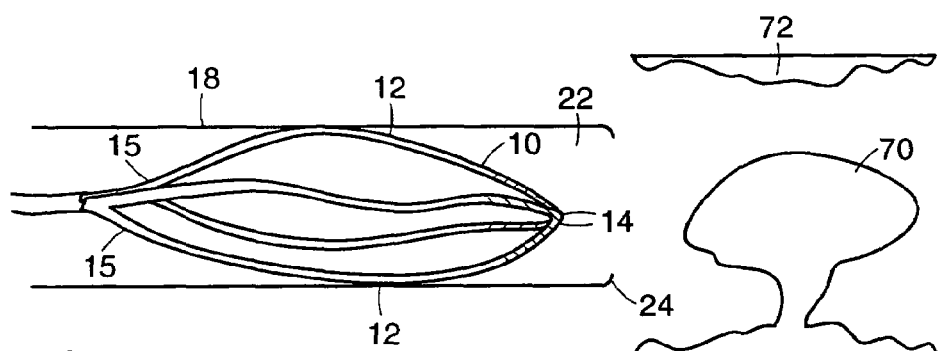
FIGS. 8A-8D are diagrammatic representations of another clinical application of a device according to the invention wherein the basket loops excise a tissue.
Figure 8B:
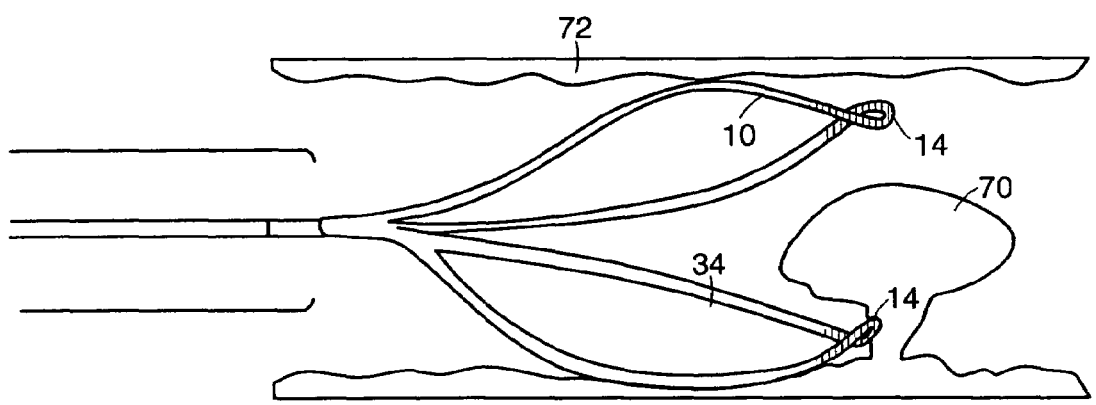
Figure 8C:
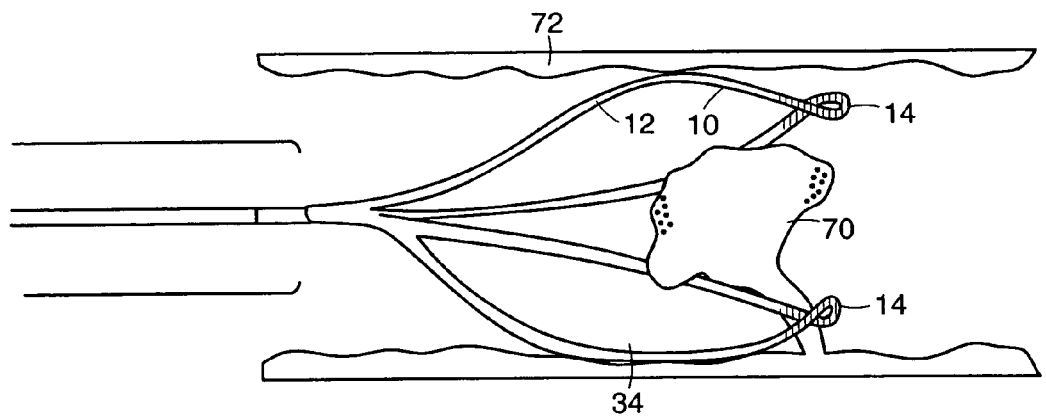
Figure 8D:
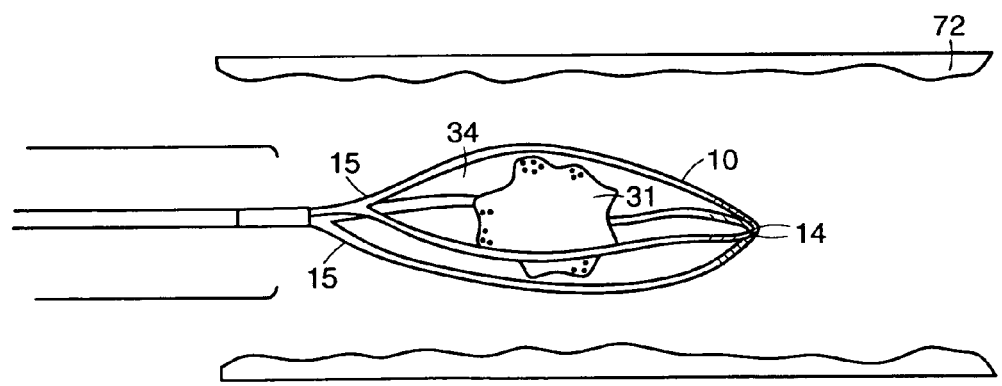

Referring to FIG. 8A, in yet another embodiment of the invention, the basket loops may be used to excise tissue (i.e., perform a biopsy procedure), for example a polyp 70 in the lumen of the gastrointestinal tract 72. An advantage of this embodiment of the invention is that the polyp 70 is preserved in the basket lumen following polypectomy in a condition suitable for subsequent pathological examination. In one embodiment, the basket loops are energized, for example, at the unattached ends 14 of the basket loops 12. In operation, as shown in FIG. 8A, the retrieval device is advanced into the lumen of the gastrointestinal tract 72, preferably under endoscopic guidance, until the basket 10 approaches the polyp 70. The polyp is end-encapsulated when the basket 10, in the open position, is advanced over the polyp as illustrated in FIG. 8B. The polyp 70 is captured within the basket lumen 34 as shown in FIG. 8C, and the basket 10 is moved to a substantially closed position. Sufficient energy by any means known to one skilled in the art is applied to the unattached ends 14 of the basket loops 12. Alternatively, the basket loops may have a cutting surface to permit excision of the polyps. Sufficient energy is applied to the unattached ends 14 of the basket loops to separate the polyp 70 from its stalk. Referring to FIG. 8D, the polyp 70, detached from the body, drops into the basket lumen 34. The polyp 70 within the basket lumen 34 is withdrawn from the gastrointestinal tract 72. The polyp may be removed from the basket for subsequent pathological analysis.

Figure 9A:
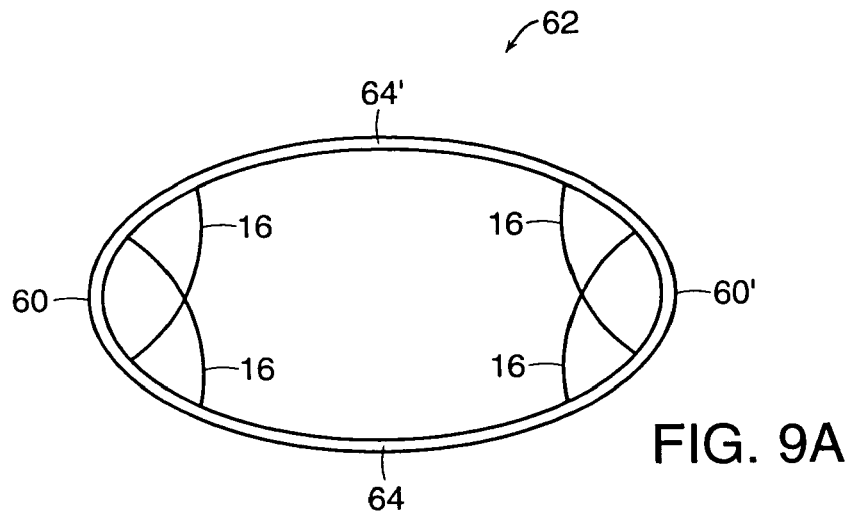
FIGS. 9A-9E illustrate a method for constructing a basket according to the invention.
Figure 9B:
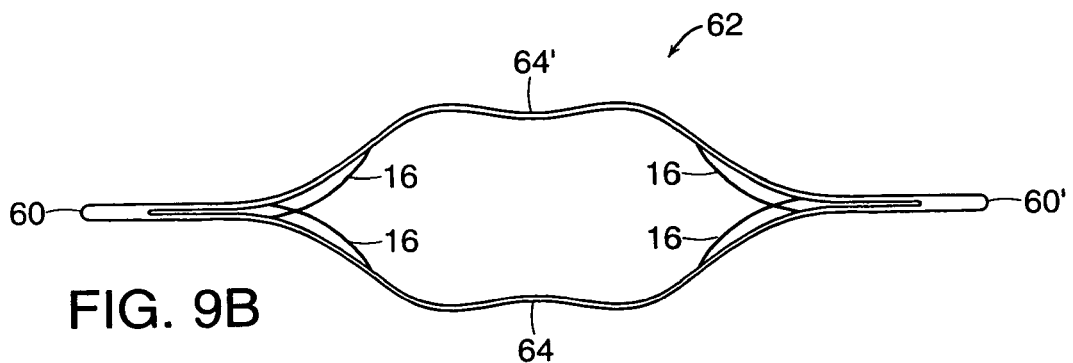
Figure 9C:
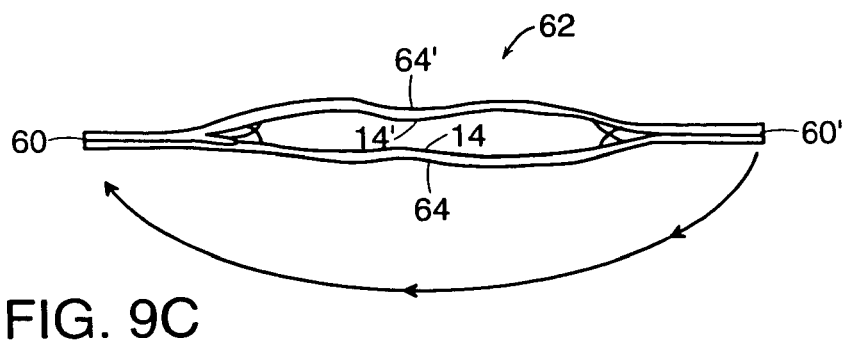

The basket loops can be constructed according to the invention from a single piece of material. Referring to FIG. 9A, a template 62 can be created from the unitary piece of material, and the template can be substantially oval and symmetrical with two oppositely disposed ends, 60 and 60', two loop members 64 and 64', and support members 16. The template 62 is removed from a single piece of substantially flat material by cutting, etching, stamping, extruding, or removing by any other method known to one skilled in the art for constructing a template from a single piece of material. Referring to a particularly preferred embodiment of the invention shown in FIG. 9B, following construction of the template 62, the ends 60, 60' of the template 62 are brought together to superimpose the ends on one another as indicated by the arrows in the side view of the template illustrated in FIG. 9C. The ends are then secured to one another thereby forming the three dimensional basket structure illustrated in FIG. 9D with the two loops. That is, the members 64, 64' become the basket loops, as illustrated in FIG. 9D.

Figure 9E:
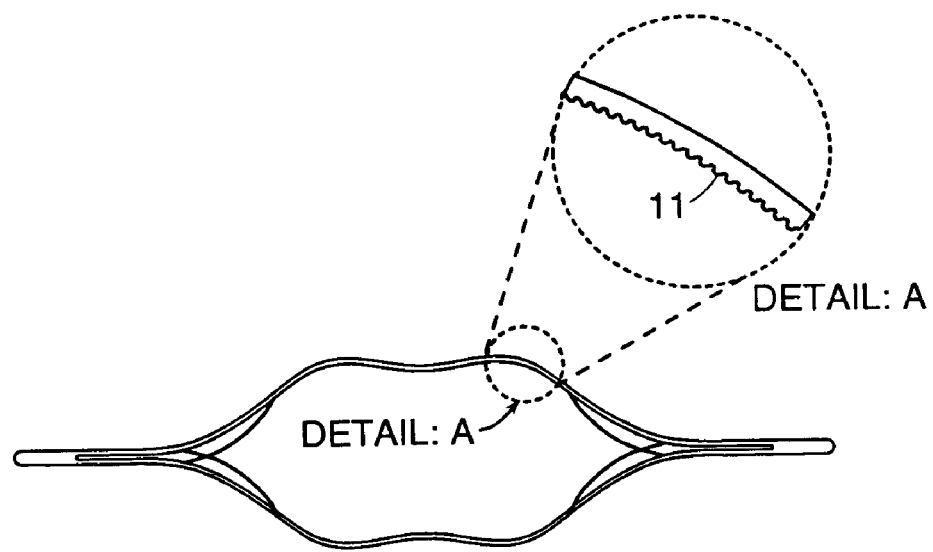
Figure 9D:
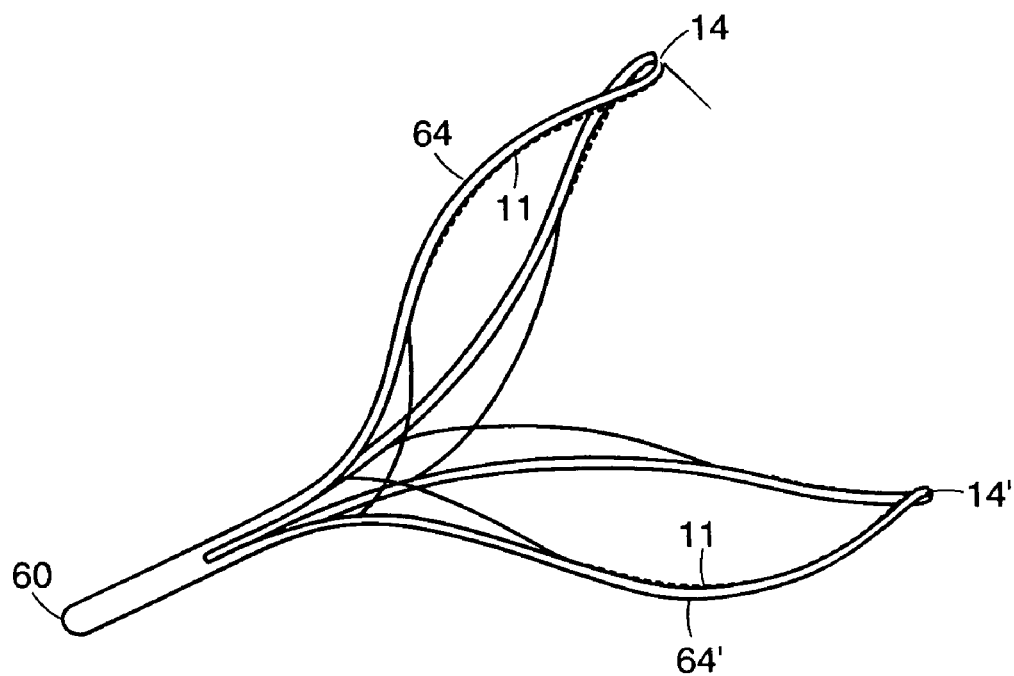

The inner surface 11 of basket loops 64 and 64' may be roughened, for example, by serrations or teeth (as shown in FIG. 9E), etched surfaces, or points. One or more of the basket loops may have such a rough inner surface. The roughened surface may be incorporated in the template as it is cut, etched, extruded or stamped from a material. Alternatively, the roughened surface may be applied after the template is constructed but before the template is folded into a three-dimensional basket. The inner surfaces 11 of the loop members 64, 64' can instead or additionally treated with an anti-slip material such as a plastic composite or a rubberized coating before the template is folded into a three dimensional basket shape with loops.

Variations, modifications, and other implementations of what is described herein will occur to those of ordinary skill in the art without departing from the spirit and the scope of the invention as claimed. Accordingly, the invention is to be defined not by the preceding description but instead by the spirit and scope of the following claims.

What is claimed is:

1. A medical device, comprising:
a proximal handle;
a sheath extending distally from the handle and having a lumen extending therethrough from a distal end of the sheath to a proximal end of the sheath; and
at least two opposing loops having a collapsed position in which the loops are collapsed within the lumen of the sheath and another position in which the loops extend from the distal end of the sheath and out of the lumen, the loops being formed from a single piece of material and joined at their proximal ends and unattached to each other at their distal ends, the loops being moveable between an open position and a closed position with the loops being closer together at their distal ends when in the closed position than when in the open position to allow capture and release of material, at least one loop including an inner surface facing an opposing loop, at least a portion of the inner surface comprising a cutting surface.

2. The device of claim 1, wherein the cutting surface comprises an energizeable surface.

3. The device of claim 2, wherein the energizeable surface is energized by RF energy.

4. The device of claim 1, wherein the cutting surface comprises at least part of the distal end of the loop.

5. The device of claim 1, wherein the sheath moves relative to the loops.

6. The device of claim 1, further comprising an elongated member extending from the handle through the lumen of the sheath, and joined to the loops.

7. The device of claim 1, wherein the loop includes a single continuous wire without further structure distal to the single continuous wire.

8. The device of claim 1, wherein one of the loops is longer than another loop.

9. A method for retrieving biological materials from a body, comprising:
inserting a medical retrieval device into a body, the device comprising a proximal handle, a sheath extending distally from the handle and having a lumen extending therethrough from a distal end of the sheath to a proximal end of the sheath, and at least two opposing loops having a collapsed position in which the loops are collapsed within the lumen of the sheath and another position in which the loops extend from the distal end of the sheath and out of the lumen, the loops being formed from a single piece of material and joined at their proximal ends and unattached to each other at their distal ends, the loops being moveable between an open position and a closed position with the loops being closer together at their distal ends when in the closed position than when in the open position to allow capture and release of material, at least one loop including an inner surface facing an opposing loop, at least a portion of the inner surface comprising a cutting surface;
placing the loops in the position in which they extend from the distal end of the sheath and out of the lumen of the sheath;
capturing a biological material within the loops; and
withdrawing the device from the body to remove the biological material from the body.

10. The method of claim 9, wherein the capturing step further comprises breaking the biological material into two or more pieces within the loops.

11. The method of claim 9, wherein the step of capturing the biological material comprises capturing a calculus or a stone.

12. The method of claim 9, wherein the step of capturing the biological material comprises capturing one of a kidney stone, a ureteral stone, a urinary bladder stone, a gall bladder stone, and a stone within the biliary tree.

13. The method of claim 9, further including energizing a portion of the cutting surface with RE energy.

14. The method of claim 9, wherein at least one of the steps of placing the loops and capturing a biological material includes moving the sheath relative to the loops.

15. The method of claim 9, wherein at least one of the steps of placing the loops and capturing a biological material includes moving an elongated member disposed within the lumen of the sheath, the medical retrieval device further including at least one wire operably attached to at least one loop and to the elongated member.

16. The method of claim 9, wherein the medical retrieval device further includes one or more support members disposed between the loops.

17. The method of claim 9, wherein the step of capturing the biological material comprises a polypectomy.

18. The method of claim 9, wherein the step of capturing the biological material comprises a biopsy procedure.

19. The method of claim 9, further including cutting the biological material from the body.

20. The method of claim 19, wherein the biological material comprises a polyp and the cutting step includes cutting a polyp stalk.

21. The method of claim 9, wherein the loop includes a single continuous wire without further structure distal to the single continuous wire.

22. The method of claim 9, wherein one of the loops is longer than another loop.

23. A medical device, comprising:
a proximal handle;
a sheath extending distally from the handle and having a lumen extending therethrough from a distal end of the sheath to a proximal end of the sheath; and
at least two opposing loops having a collapsed position in which the loops are collapsed within the lumen of the sheath and another position in which the loops extend from the distal end of the sheath and out of the lumen, the loops being formed from a single piece of material and joined at their proximal ends and unattached to each other at their distal ends, the loops being moveable between an open position and a closed position with the loops being closer together at their distal ends when in the closed position than when in the open position to allow capture and release of material, at least one of the loops comprising a cutting surface, and wherein the loop includes a single continuous wire without further structure distal to the single continuous wire.

24. The device of claim 23, wherein the cutting surface comprises an energizeable surface.

25. The device of claim 23, wherein the cutting surface comprises at least part of the distal end of the loop.

26. The device of claim 23, further comprising an elongated member extending from the handle through the lumen of the sheath, and joined to the loops.

27. The device of claim 23, wherein at least a portion of the loops is coated with an anti-slip substance.

28. The device of claim 23, wherein at least a portion of the loops is roughened.

29. The device of claim 23, further comprising one or more support members disposed between the loops.

30. The device of claim 23, further comprising at least one wire operably attached to at least one loop and to the elongated member, movement of the loops between the closed and open positions being achieved through movement of the elongated member.

31. The device of claim 23, wherein one of the loops is longer than another loop.

32. A method for retrieving biological materials from a body, comprising:
   inserting a medical retrieval device into a body, the device comprising a proximal handle, a sheath extending distally from the handle and having a lumen extending therethrough from a distal end of the sheath to a proximal end of the sheath, and at least two opposing loops having a collapsed position in which the loops are collapsed within the lumen of the sheath and another position in which the loops extend from the distal end of the sheath and out of the lumen, the loops being formed from a single piece of material and joined at their proximal ends and unattached to each other at their distal ends, the loops being moveable between an open position and a closed position with the loops being closer together at their distal ends when in the closed position than when in the open position to allow capture and release of material, at least one of the loops comprising a cutting surface, and wherein the loop includes a single continuous wire without further structure distal to the single continuous wire;
   placing the loops in the position in which they extend from the distal end of the sheath and out of the lumen of the sheath;
   capturing a biological material within the loops; and
   withdrawing the device from the body to remove the biological material from the body.

33. The method of claim 32, wherein the capturing step further comprises breaking the biological material into two or more pieces within the loops.

34. The method of claim 32, wherein the step of capturing the biological material comprises capturing a calculus or a stone.

35. The method of claim 32, further including energizing a portion of the cutting surface with RF energy.

36. The method of claim 32, wherein at least one of the steps of placing the loops and capturing a biological material includes moving an elongated member disposed within the lumen of the sheath, the medical retrieval device further including at least one wire operably attached to at least one loop and to the elongated member.

37. The method of claim 32, wherein the medical retrieval device further includes one or more support members disposed between the loops.

38. The method of claim 32, wherein one of the loops is longer than another loop.

39. A medical device, comprising:
   a proximal handle;
   a sheath extending distally from the handle and having a lumen extending therethrough from a distal end of the sheath to a proximal end of the sheath; and
   at least two opposing loops having a collapsed position in which the loops are collapsed within the lumen of the sheath and another position in which the loops extend from the distal end of the sheath and out of the lumen, the loops being formed from a single piece of material and joined at their proximal ends and unattached to each other at their distal ends, the loops being moveable between an open position and a closed position with the loops being closer together at their distal ends when in the closed position than when in the open position to allow capture and release of material, at least one of the loops comprising a cutting surface, and the at least two opposing loops consisting essentially of two opposing loops.

40. The device of claim 39, wherein the cutting surface comprises an energizeable surface.

41. The device of claim 39, wherein the cutting surface comprises at least part of the distal end of the loop.

42. The device of claim 39, further comprising an elongated member extending from the handle through the lumen of the sheath, and joined to the loops.

43. The device of claim 39, wherein at least a portion of the loops is coated with an anti-slip substance.

44. The device of claim 39, wherein at least a portion of the loops is roughened.

45. The device of claim 39, further comprising one or more support members disposed between the loops.

46. The device of claim 39, further comprising at least one wire operably attached to at least one loop and to the elongated member, movement of the loops between the closed and open positions being achieved through movement of the elongated member.

47. The device of claim 39, wherein the loop includes a single continuous wire without further structure distal to the single continuous wire.

48. The device of claim 39, wherein one of the loops is longer than another loop.

49. A method for retrieving biological materials from a body, comprising:
   inserting a medical retrieval device into a body, the device comprising a proximal handle, a sheath extending distally from the handle and having a lumen extending therethrough from a distal end of the sheath to a proximal end of the sheath, and at least two opposing loops having a collapsed position in which the loops are collapsed within the lumen of the sheath and another position in which the loops extend from the distal end of the sheath and out of the lumen, the loops being formed from a single piece of material and joined at their proximal ends and unattached to each other at their distal ends, the loops being moveable between an open position and a closed position with the loops being closer together at their distal ends when in the closed position than when in the open position to allow capture and release of material, at least one of the loops comprising a cutting surface, and the at least two opposing loops consisting essentially of two opposing loops;
   placing the loops in the position in which they extend from the distal end of the sheath and out of the lumen of the sheath;
   capturing a biological material within the loops; and
   withdrawing the device from the body to remove the biological material from the body.

50. The method of claim 49, wherein the cutting surface comprises an energizeable surface.

51. The method of claim 49, wherein the cutting surface comprises at least part of the distal end of the loop.

52. The method of claim 49, further comprising an elongated member extending from the handle through the lumen of the sheath, and joined to the loops.

53. The method of claim 49, wherein at least a portion of the loops is coated with an anti-slip substance.

54. The method of claim 49, wherein at least a portion of the loops is roughened.

55. The method of claim 49, further comprising one or more support members disposed between the loops.

56. The method of claim 49, further comprising at least one wire operably attached to at least one loop and to the elongated member, movement of the loops between the closed and open positions being achieved through movement of the elongated member.

57. The method of claim 49, wherein the loop includes a single continuous wire without further structure distal to the single continuous wire.

58. The method of claim 49, wherein one of the loops is longer than another loop.

* * * * *

UNITED STATES PATENT AND TRADEMARK OFFICE
CERTIFICATE OF CORRECTION

PATENT NO. : 7,678,118 B2  Page 1 of 1
APPLICATION NO. : 11/221831
DATED : March 16, 2010
INVENTOR(S) : James S. Bates et al.

It is certified that error appears in the above-identified patent and that said Letters Patent is hereby corrected as shown below:

Claim 13, column 10, line 12, "RE energy" should read -- RF energy --.

Signed and Sealed this

Fourth Day of May, 2010

David J. Kappos
*Director of the United States Patent and Trademark Office*